United States Patent [19]

Mace et al.

[11] Patent Number: 4,958,075
[45] Date of Patent: Sep. 18, 1990

[54] GAS ANALYZER

[75] Inventors: Leslie E. Mace, Mercer Island; Daniel W. Knodle, Seattle; Lawrence L. Labuda, Issaquah, all of Wash.; Philip F. Nuzzo, Wallingford, Conn.

[73] Assignee: NTC Technology Inc., Wilmington, Del.

[21] Appl. No.: 453,227

[22] Filed: Dec. 14, 1989

Related U.S. Application Data

[63] Continuation of Ser. No. 107,267, Oct. 9, 1987, abandoned.

[51] Int. Cl.$^5$ ............... A61B 5/097; G01N 21/05; G01N 21/61
[52] U.S. Cl. ............................ 250/343; 128/719
[58] Field of Search ............ 250/343; 128/664, 719, 128/202.22, 204.22, 207.18; 422/91, 98; 436/171

[56] References Cited

U.S. PATENT DOCUMENTS

| | | | |
|---|---|---|---|
| 4,067,329 | 1/1978 | Winicki | 128/202.22 |
| 4,155,357 | 5/1979 | Dahl | 128/202.22 |
| 4,578,762 | 3/1986 | Wong | 364/497 |
| 4,648,396 | 3/1987 | Raemer | 128/204.22 |
| 4,649,711 | 3/1987 | Sibley et al. | 62/129 |
| 4,859,858 | 8/1989 | Knodle et al. | 250/504 R |
| 4,859,859 | 8/1989 | Knodle et al. | 250/504 R |

OTHER PUBLICATIONS

Brochures, Cascadia Technology Corporation and Novametrix [undated].

*Primary Examiner*—Constantine Hannaher
*Attorney, Agent, or Firm*—Hughes & Multer

[57] ABSTRACT

Sampling attachments or systems for infrared gas analyzers of the non-dispersive type. Major components of the system include a sampling device or cuvette, a vacuum pump for effecting a flow of the gases to be analyzed through the cuvette, a microprocessor based pump control, and a switch which is closed and allows the pump to be turned on only if an appropriate sampling cuvette is connected up to the pump. The sampling attachments are designed for medical applications—to provide readings of tidal carbon dioxide, for example. They have a minimally invasive nasal cannula for collecting the gases which are to be subjected to analysis; viz., those exhaled by a patient. These gases are conducted to the cuvette through a line which is gastight but allows moisture to escape, thereby keeping moisture mixed with the gases being analyzed from corrupting the readings outputted by the gas analyzer. The attachment can be easily and quickly disassembled and the components disposed of or sterilized and recycled if they become contaminated. Provision is made for collecting the gases after they have been discharged from the cuvette so that they will not be discharged into and perhaps contaminate the ambient surroundings.

16 Claims, 3 Drawing Sheets

GAS ANALYZER

This is a continuation of co-pending application Ser. No. 107,267, filed on Oct. 9, 1987, now abandoned.

TECHNICAL FIELD OF THE INVENTION

In one aspect, the present invention relates to novel, improved apparatus for measuring the amount or proportion of one gas in a mixture of gases.

And in yet another aspect, the present invention relates to novel, improved sampling units for gas analyzers as described in the preceding paragraph.

BACKGROUND OF THE INVENTION

Copending application Nos. 024,769 and 024,770, both filed Mar. 11, 1987, (and issued on Aug. 22, 1989 as Pat. Nos. 4,859,859 and 4,859,858, respectively) disclose novel gas analyzers of the non-dispersive type which operate on the premise that the concentration of a designated gas can be measured: (1) by passing a particularized beam of infrared radiation through the gas, (2) and ascertaining the attenuation of the energy in a narrow band absorbable by the designated gas with a detector capable of generating an attenuation proportional electrical output signal.

Medical applications of these gas analyzers are among the more important and perhaps the most significant of these is the monitoring of tidal carbon dioxide, i.e., the concentration of carbon dioxide in a patient's exhalations.

This expired carbon dioxide level can be employed by medical personnel to control the operation of a mechanical ventilator hooked up to the patient to assist him in breathing. In certain major surgical procedures, the ventilator completely takes over the breathing function for the patient.

In a typical medical application of the gas analyzers just described, an airway adapter is employed to connect a tube inserted into the patient's trachea to the plumbing of a mechanical ventilator (not shown). The airway adapter also confines the expired gases to a flow path with a precise, transverse dimension; and it furnishes an optical path between an infrared radiation emitter and an infrared radiation detector unit, both components of an infrared transducer.

The infrared radiation traverses the gases in the airway adapter where it is attenuated because part of the radiation is absorbed by the designated gas being analyzed. The attenuated beam of infrared radiation is then filtered to eliminate energy of frequencies lying outside a narrow band which is absorbed by the gas being measured. The infrared radiation in that band impinges upon a detector which consequentially generates an electrical signal proportional in magnitude to the intensity of the infrared radiation impinging upon it.

This novel arrangement allows the analysis to be performed at a location immediately adjacent the patient instead of the samples being transmitted to a more remote location for analysis as is commonly done in other gas analyzers. This is an advantage because distortion attributable to the transmission of the sample to the remote location is eliminated. Also eliminated are problems commonly encountered with the lines through which the sample is routed—poor dynamic response, water in the line, etc.

Nevertheless, the system just described has the disadvantage that it is useful only in those applications in which the patient is being intubated; i.e., assisted in breathing or breathed for by a mechanical ventilator. There still exists, as a consequence, a need for gas analyzers with the advantages and attributes of those described in the preceding paragraph but of greater utility in circumstances where the patient is breathing satisfactorily on his own and therefore does not require intubation but is in a situation where it is necessary or advantageous to monitor his breathing. One example is where a local anesthetic is being administered. In these and comparable situations, it is highly desirable to avoid the trauma involved in installing a tracheal tube as would be required if the previously disclosed gas analyzer apparatus were employed.

SUMMARY OF THE INVENTION

We have now invented, and disclosed herein, a novel gas sampling system or attachment which allows gas analyzers as described in the above-cited copending applications to be employed to monitor a patient's breathing without the patient having to undergo the considerable trauma associated with inserting a tube into his trachea.

Generally speaking, this novel system consists of a nasal cannula through which the patient exhales. The expired breath is transmitted through a line—preferably fabricated of a material which is gastight but will allow moisture to escape—to a sampling device or cuvette as we term it.

As the patient's exhalations pass through the cuvette, they are intercepted by a beam of infrared radiation with a wavelength such that the infrared radiation will be absorbed by the gas being monitored (typically carbon dioxide). The attenuation of the infrared radiation is measured as described in the above-cited copending applications and employed to generate a signal indicative of the concentration of carbon dioxide in the patient's expirations.

The downstream side of the cuvette is connected through a line with a moisture trap incorporated in it to a vacuum pump which effects a flow of the patient's expired breath through the sampling cuvette. This pump causes the gases being analyzed to flow through the cuvette. It therefore serves the same function as the mechanical ventilator to which the airway adapter disclosed in the above-cited copending applications is coupled.

Gas discharged from the pump can be collected via a pump discharge line and treated so that contaminants in those gases will not be dumped into the surrounding environs.

Associated with the vacuum pump is a switch which must be closed before the pump can be turned on. This switch is closed only when the cuvette-to-pump line is connected. It therefore ensures that the pump will operate only when a sampling system as disclosed herein is being employed in the gas analyzer in lieu of the airway adapter used when the patient is intubated.

The closing of the foregoing switch also causes a microprocessor incorporated in the system to enter a different routine. Among other things, this routine compensates for differences in the readings outputted by the gas analyzer that are attributable to the subatmospheric pressure in the sampling system rather than in the pressure level of the gas being monitored. The microprocessor will also turn the pump off if flow is interrupted due to a kink in a line, for example, to prevent mechanical damage. At the same time, it will activate a signal, alerting the operator so that he can correct the problem.

Also associated with the pump and disposed in line between it and the sampling cuvette is a pressure transducer. The signals available from this transducer can be employed for two important purposes. One is to identify mechanical failures in the sampling system such as a kinked line or occlusion. Also, the signals from the pressure transducer can be used to provide pressure compensation as described in the preceding paragraph and thereby produce a more accurate measurement of the gas being monitored.

In relation to currently available competitive devices, the novel sampling systems disclosed herein have the advantage that the sampling cuvette can be located very close to the patient. As a consequence, the samples are monitored only a short distance away from the point of origin of the gases being monitored. This eliminates the excessively long small diameter tubes and the moisture traps employed in conventional systems to conduct the samples to a remotely located monitoring station. This arrangement is undesirable because of the inaccuracies introduced by time delays, moisture in the tube, low dynamic responses, etc.

Another advantage of our novel sampling system is that it is easily disassembled by simple twist-type fittings into components which can be disposed of or sterilized and replaced if they become contaminated.

A final important feature of the novel sampling systems described herein is a clip for attaching the sampling cuvette to a patient's clothing or his bedclothing, etc. This can be used to keep a strain from being imposed on the nasal cannula and: causing discomfort to the patient and/or pulling the cannula off its connecting line.

OBJECTS OF THE INVENTION

From the foregoing, it will be apparent to the reader that one important object of the present invention resides in the provision of novel, improved sampling systems for gas analyzers.

A related and also primary and important object of the invention is the provision of sampling systems in accord with the preceding object which are intended for gas analyzers designed for medical applications and which allow such gas analyzers to be used to monitor a subject's tidal carbon dioxide level (or other gas in his exhalations) without employing the traumatic procedure of placing a tube in the subject's trachea.

Other also important but more specific objects of our invention reside in the provision of sampling systems as described in the preceding object:

which can be easily and quickly disassembled into components that are disposable and can alternatively be sterilized and reused if they become contaminated;

which collect a subject's exhalations by way of a minimally invasive nasal cannula instead of a tracheal tube;

which are resistant to contamination by moisture mixed with the gases being sampled;

which include a vacuum pump for effecting a flow of the gases being sampled through the system;

which, in conjunction with the preceding object, have a control system which allows the vacuum pump to be turned on only if a flow system which is specifically adapted to be connected to a vacuum pump (and not to an external pump such as a ventilator) is connected to the vacuum pump;

which, in conjunction with the last object but one, have a control system which is designed to shut off the pump and to activate an operator alerting signal if flow through the system is interrupted;

which provide compensation in the readings outputted from the gas analyzer for the below atmospheric partial pressures in the sampling system;

in which provision is made for separating out moisture before the gases are analyzed, thereby keeping moisture mixed with the gases from corrupting the readings outputted by the gas analyzer in which the sampling attachment is incorporated;

in which provision is made for collecting the sampled gases and thereby keeping them from being discharged into and perhaps contaminating the ambient surroundings;

in which the analysis of the gases being analyzed is performed at a location near the point of collection of those gases, thereby eliminating the time delay, contamination, and poor dynamic response problems appurtenant to those heretofore proposed systems in which the gases are transmitted to and analyzed at a location removed from the location where the gases are collected; and in which provision is made for relieving strains that might otherwise be imposed, thereby eliminating discomfort to the patient and/or damage to the system that might result from the imposition of such strains.

Other important objects and features and additional advantages of our invention will be apparent to those skilled in the relevant arts from the foregoing and the appended claims and as the ensuing detailed description and discussion proceeds in conjunction with the accompanying drawing.

DETAILED DESCRIPTION OF THE INVENTION

Figure 1:
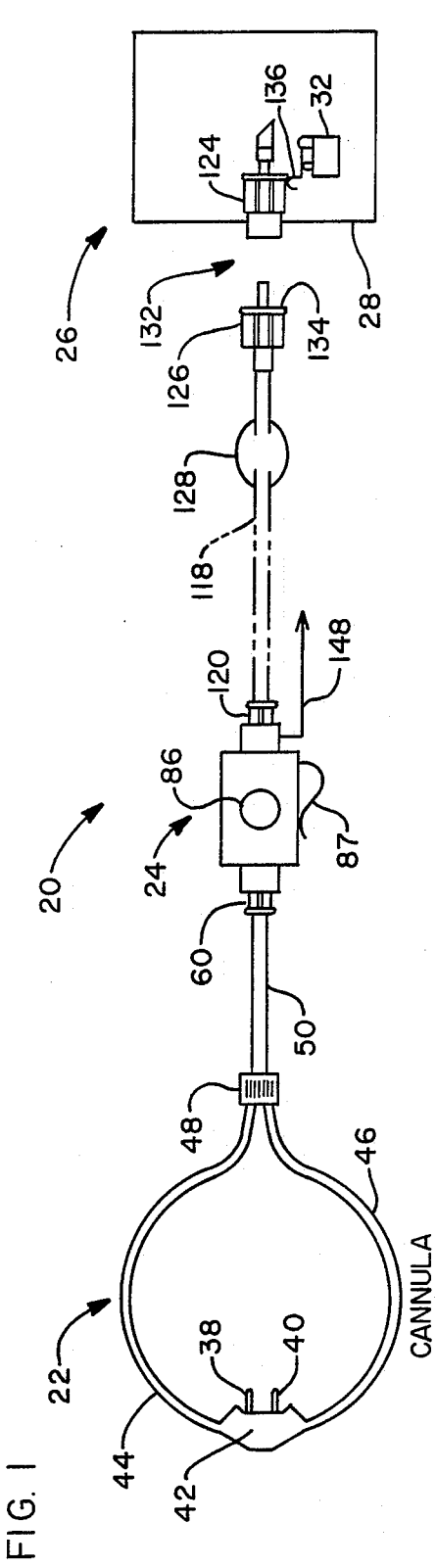
FIG. 1 is a somewhat pictorial view of a gas analyzer sampling attachment or system which embodies the principles of the present invention.

Referring now to the drawing, FIG. 1 depicts a gas sampling system or attachment 20 constructed in accord with, and embodying, the principles of the present invention. As discussed above, this attachment is designed to be used with a non-dispersive, infrared as analyzer in medical applications—typically to measure a patient's tidal carbon dioxide level. Major components of sampling system 20 include a nasal cannula 22; a sampling device 24; and a unit 26 consisting of a casing 28 in which a vacuum pump 30, switch 32, and microprocessor 34 are housed.

Cannula 22 collects the gases exhaled by the patient, and the concentration of carbon dioxide in those gases is ascertained as the gases flow through sampling device 24. Vacuum pump 30 effects the flow of the gases being sampled through sampling device 24, and the closing of switch 32 conditions microprocessor 34 to run those routines which are appropriate to a sampling device of the character disclosed herein. The closing of that switch also conditions a pump control circuit 36. As a consequence, pump 30 can be turned on only if a sampling attachment of the character disclosed herein is connected up to that pump.

Nasal cannula 22 is a smaller version of commercially available components. It includes two pronglike tubes 38 and 40 which are designed to be inserted in the patient's nostrils. These tubes communicate with a plenum 42. Gases exhaled by the patient flow into tubes 38 and 40 and, from those components, through plenum 42 and lines 44 and 46, a fitting 48, and a line 50 to sampling device 24.

The accuracy of the measurements outputted by the gas analyzer equipped with sampling attachment 20 can be adversely affected by the condensation of moisture in sampling device 24. To forestall such condensation, line 50 will preferably be fabricated from a material which is permeable as far as water vapor is concerned but impermeable with respect to the other gases flowing through it to sampling device 24. One such, and appropriate, material (Nafion) is manufactured by Perma Pure Products, Inc., Toms River, N.J. Nafion and similar tubing also has the advantage that it does not decrease the dynamic response of the sampling system as would a conventional moisture trap.

As suggested in FIG. 1, the sampling device 24 of system 20 is located very close to the point-of-collection of the gases being sampled; viz., nasal cannula inlet tubes 38 and 40. As discussed above, this gives sampling attachment 20 a number of significant advantages over heretofore available, competing devices in which the sample is collected and typically transmitted to a location many feet away before it is analyzed. Problems arise in these prior art systems because of the delay between the time the gases being analyzed are collected and the time they arrive at the station where they are analyzed. Also, condensation in tubes of the length employed in the prior art devices causes problems as does the poor dynamic response attributable to the long lines of the prior art devices.

Figure 3:
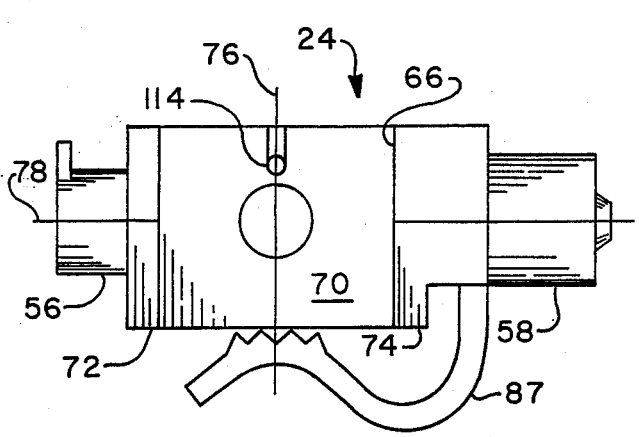
FIG. 3 is a side view of a sampling device employed in the attachment of FIG. 1.
Figure 4:
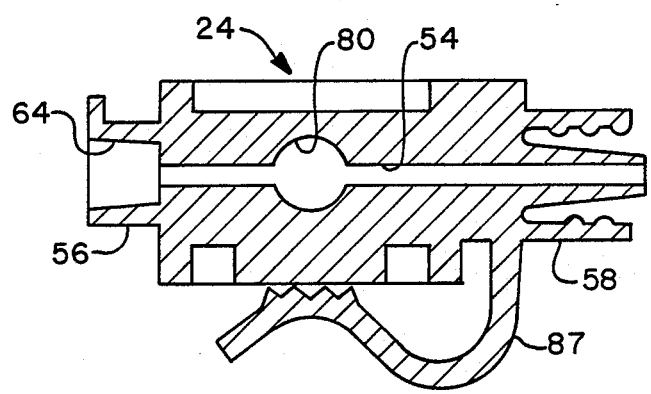
FIG. 4 is a section through the sampling device.

Referring now to FIGS. 3-6, it is the function of sampling device 24 to confine the gases being analyzed to a precisely located and dimensioned flow path. As the gases flow along that path, a beam of infrared radiation from the emitter of a transducer such as that identified by reference character 52 in FIG. 4 is directed through the sample of gases being analyzed.

After passing through that body of gases, the beam of infrared radiation is passed through a filter. That filter absorbs all of the radiation except for that in a narrow band centered on a frequency which is absorbed by the gas of concern. This narrow band radiation falls on a detector, producing an electrical output signal proportional in magnitude to the magnitude of the infrared radiation impinging upon the detector. By comparing this signal with one indicative of the emitted energy in the band of interest, one can derive a signal which represents the energy absorbed by the gas of concern. The difference signal is in turn proportional to the concentration of that gas in the sample being analyzed.

Figure 6:
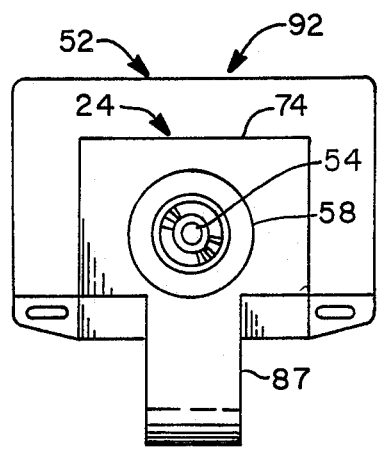
FIG. 6 is a view showing the infrared transducer assembled to the sampling device.
Figure 5:
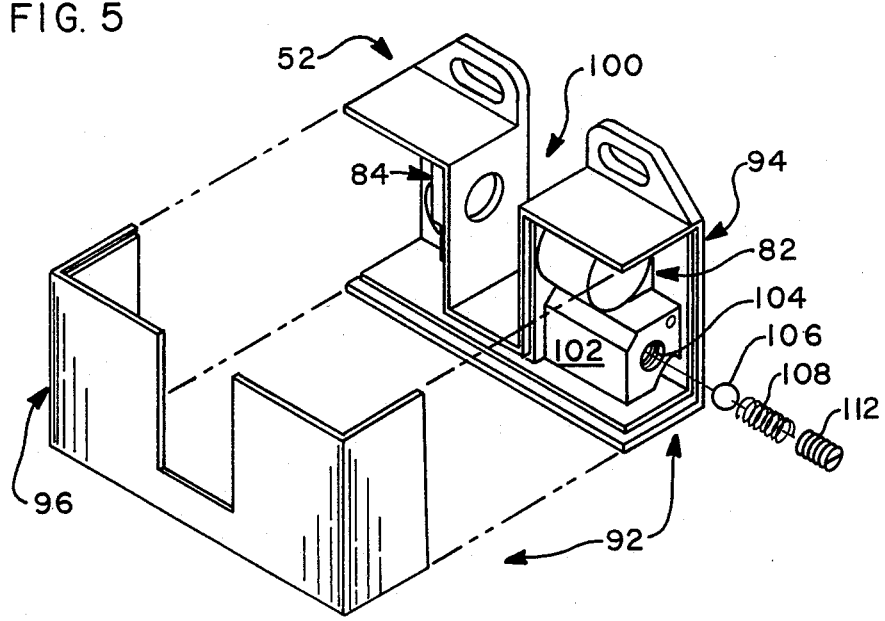
FIG. 5 is an exploded view of an infrared transducer which can be employed in conjunction with the sampling device of FIG. 3 to generate a signal indicative of the concentration of a gas flowing through the sampling device.

Turning now to FIGS. 3, 5, and 6, the illustrated sampling device or cuvette 24 is a one-piece unit typically molded from an ABS polymer. ABS and comparable polymers are preferred because they provide the ruggedness required by a suitable cuvette. Also, cuvettes can be molded to extremely close tolerances and consistent, reproducible dimensions from such polymers. This is necessary because the intensity of the infrared radiation impinging upon the detector of infrared transducer 52 is dependent upon the length of the path between its emitter and the detector, and the length of that path is controlled by the width of the sampling cuvette. Consequently, unless consistently reproducible tolerances are maintained, calibration of each individual sampling cuvette 24 would be required; and this might be impractical at worst and economically prohibitive at best. Furthermore, sampling cuvettes of the illustrated configuration and fabricated from polymers ABS and comparable are relatively inexpensive. Consequently, they can be disposed of after being used although sterilization and reuse of this component is by all means a practical approach.

Sampling cuvette 24 is of a generally parallelepipedal configuration, and it has a bore or sampling passage 54 of small diameter extending rectilinearly from end-to-end therethrough.

At the opposite ends of cuvette 24 are integral bosses 56 and 58 to which components 60 and 62 of conventional Luer fittings can be attached (see FIG. 1).

Luer fitting 60 component is attached to the downstream end of line 50 and is employed to detachably connect that line to sampling device 24. Connected, line 50 communicates with the sampling passage 54 of cuvette 24 via a passage 64 through the integral, upstream boss 56 of the sampling device.

Mounting recesses for transducer 52 are formed on opposite sides of sampling cuvette 24. One of these recesses is shown in FIG. 3 and identified by reference character 66. Mounting recesses 66 furnish transducer embraced support surfaces 70 at the inner ends of the recesses, and there are flanges 72 and 74 at the opposite ends of each recess. These flanges and support surfaces 70 accurately position the transducer relative to the sampling cuvette when the transducer and cuvette are assembled.

Sampling cuvette 24 is symmetrical with respect to centerplane 76 (shown edge-on in FIG. 3). This is important from a practical viewpoint because transducer 52 can consequentially be assembled to sampling device 24 in the orientation shown in FIG. 6; or it can be turned end-for-end and still be assemblable to the device. Consequently, in addition to its other advantages discussed above, sampling cuvette 24 is user friendly.

An aperture 80 extending transversely through sampling adapter 24 provides an optical path from the infrared radiation emitter 82 of transducer 52 and the gases in sampling passage 54 to the infrared radiation detector 84 of the transducer. Aperture 80 has a relatively large diameter compared to the apertures in the most comparable components of heretofore proposed gas analyzers.

The diameter of the transverse passage 80 providing the optical path through sampling cuvette 24 is also much longer than the diameter of sampling passage 54.

The latter passage is purposely kept small to accommodate a sampling device inlet line 50 with an internal diameter which is compatible with the near capillary diameters of the passages in the various tubes of nasal cannula 22.

To keep the gases in sampling passage 54 from escaping through aperture 80, the opposite ends of that aperture are sealed by sapphire windows. One of these windows is illustrated in FIG. 3 and identified by reference character 86. Sapphire windows are employed because other materials such as glass or plastic would absorb the infrared radiation to an extent that would significantly degrade the quality of the signal generated by detector 84.

Another important component of sampling device 24 is an integral clip 87 for attaching the sampling device to a patient's clothing or his bedclothes, for example. This relieves strains which might otherwise be imposed on and damage components of sampling attachment 24. The strain relief afforded by clip 87 may also minimize discomfort to the patient and keep the flow lines of the sampling attachment from becoming kinked or tangled.

The transducer 52 employed in association with sampling device 24 to provide a signal indicative of the level of a selected gas flowing through sampling passage 54 is not part of the present invention and is disclosed in detail in companion applications No. 024,769 and 024,770. That transducer will accordingly not be described in detail herein except as is necessary for an understanding of the present invention. Briefly, however, transducer 52 a includes a casing 92 composed of separate components 94 and 96 in which emitter 82 and detector 84 are housed. Defined by casing components 94 and 96 is a rectangularly sectioned recess 100 in which sampling device 24 is received in assembling transducer 52 to the sampling device.

Also housed in transducer casing 92 is a fitting 102 with a transversely extending passage 104 formed therethrough. Disposed in passage 104 are: (1) a spherical detent 106; (2) a spring 108, which biases detent 106 toward the inner end of passage 104; and (3) a plug 112. That plug is threaded into the bore 104 through fitting 102 and retains the detent and detent spring in that bore. A flange (not shown) at the inner end of passage 104 keeps detent 106 from falling out that end of the passage.

With transducer 52 assembled to sampling device 24 as shown in FIG. 6, for example, detent 106 is trapped in a complementary recess 114 in sampling device 24 (see FIG. 7) to secure the transducer to the sampling device. Detent trapping recesses are provided on opposite sides of cuvette 24 so that transducer 52 may be coupled to sampling device 24 in either of the two orientations discussed above.

Referring again to FIGS. 1 and 2, the gases discharged from sampling cuvette 24 after having been subjected to infrared analysis in the manner just described flow through a line 118 to the sampling system unit 26 in which pump 30 is housed. Line 118 is coupled to sampling cuvette by a Luer fitting which includes the integral boss 58 at the downstream end of the cuvette and a cooperating component 120 fixed to the upstream end of line 118. The opposite end of the line is coupled to a pump inlet line 122 in unit 26 by a second Luer fitting consisting of one component 124 attached to the casing 28 of unit 26 and a second component 126 which is attached to the downstream end of line 118.

This use of Luer or similar, easily decoupled fittings to join the above-discussed components of sampling system 20 together is considered a significant feature of our invention. Such fittings permit the cannula and flow line 50, sampling cuvette 24, and flow line 118 to be easily and quickly removed and replaced in the event that those components become contaminated. As discussed above, those components are inexpensive enough that it is practical to simply dispose of contaminated components. Alternatively, as also suggested above, the components in question can instead be cleaned or otherwise sterilized and reused.

Figure 2:
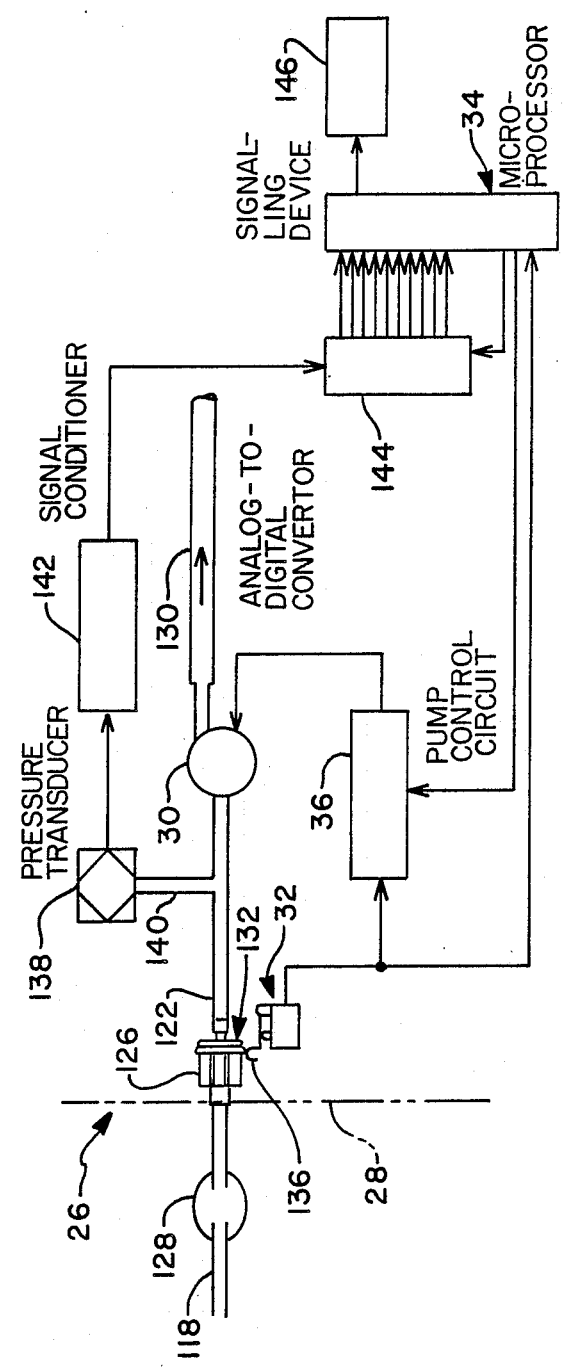
FIG. 2 is a schematic illustration of a pump, pressure monitoring, and control unit employed in the system of FIG. 1.

As shown in both FIGS. 1 and 2, a moisture trap 128 is incorporated in the flow line 118 between sampling device 24 and pump/pressure monitoring/control unit 26. This trap removes from the gases delivered to vacuum pump 30 any additional moisture which may have condensed in the gases being sampled, either in sampling device 24 or in line 118. Removing the condensate prevents possible damage to or contamination of vacuum pump 20, especially when the patient being monitored is also being given aerosol therapy or medication, for example.

The particular type of moisture trap employed in sampling attachment 20 is not critical. For that reason and because moisture traps are well known and readily available devices, it is not deemed necessary to describe that component of sampling system herein in detail.

The gases flowing from sampling device 24 through discharge line 118 are conducted through the inlet line 122 in unit 26 to vacuum pump 30. We pointed out above that pump 30 is employed to effect a flow of those gases through the sampling system. From the vacuum pump, the sampled gases are discharged into a line 130 also housed in the casing 28 of unit 26. This line can be connected to a collection and treatment system (not part of the present invention and not shown) to keep contaminated gases from being discharged into the ambient surroundings.

As mentioned briefly above, the operation of vacuum pump 30 is controlled by a conventional circuit 36. This circuit has two inputs, one from switch 32 and the other from microprocessor 34. Pump control circuit 36 cannot be activated by microprocessor 34 to turn on pump 30 unless switch 32 is closed by the installation of a sampling device of the character discussed above and identified by reference 24. In particular, when a device of that type is connected to unit 26 by coupling the discharge line attached component 126 of Luer fitting 132 to the second component 124 of that fitting, a flange 134 on the downstream end of component 126 engages and depresses switch actuator 136 to close the switch.

The information which microprocessor 34 requires to turn vacuum pump 30 on after circuit 36 is conditioned by the closing of switch 32 is acquired from a conventional pressure transducer 138 connected through a tap 140 to vacuum pump inlet line 122. The absolute pressure indicative, analog signal generate by transducer 138 is processed in a conventional signal conditioner and amplifier 142 and converted in an analog-to-digital converter 144 to a digital signal which can be acquired by microprocessor 34.

The data acquired from switch 32 when it is closed also enables another microprocessor routine which is compatible with the use of a system such as that identified by reference character 20 rather than an airway adapter system as disclosed in companion application Nos. 024,769 and 024,770, for example. That routine provides a pressure compensation which is appropriate for the subatmospheric pressures existing in sampling system 20. Other simultaneously enabled routines activate a display to confirm that a sampling system as described herein is hooked up in the gas analyzer.

Figure 7:
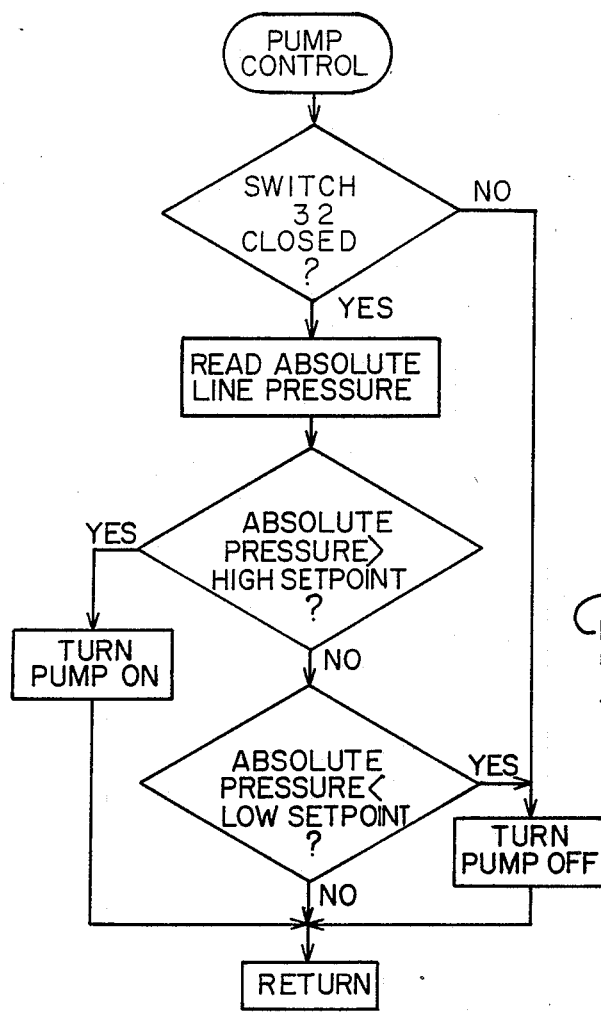
FIG. 7 is a flow diagram of a control routine run by a microprocessor employed in the unit illustrated in FIG. 2.

The routine run by microprocessor 34 in operating vacuum pump 30 is shown in flow diagram form in FIG. 7. Microprocessor 34 first checks to determine whether switch 32 is opened or closed. If that switch is open, vacuum pump 30 is turned off by microprocessor 34 if the pump is running; or, if it is not, the microprocessor keeps the pump from being turned on. If, on the other hand, switch 32 is closed, indicating that a sampling cuvette of the type identified by reference character 24 is connected to vacuum pump 30, microprocessor 34 then reads the absolute pressure in sampling attachment 20 as determined by transducer 138. If that absolute pressure is greater than a high set point—i.e., the vacuum in the sampling attachment is lower than wanted—microprocessor 34 turns vacuum pump 30 on.

If, in contrast, the vacuum is sufficiently high, microprocessor 34 checks to see whether the absolute pressure in sampling system 20 is below a low set point. If it is, microprocessor 34 turns the vacuum pump 30 off as, in this case, the pressure indicates that there is a kink or other obstruction in line 50 or line 118, and vacuum pump 30 might be damaged if it were thereafter allowed to run.

At the same time that it turns off vacuum pump 30, microprocessor 34 turns on a visual, audible, or other signaling device 146. This alerts personnel monitoring the patient and the gas analyzer that there is a condition which requires correction.

Returning again to FIG. 7, if the absolute pressure in sampling system 20 is above the low set point when that pressure is read by microprocessor 34, the loop shown in FIG. 7 is reentered.

Figure 8:
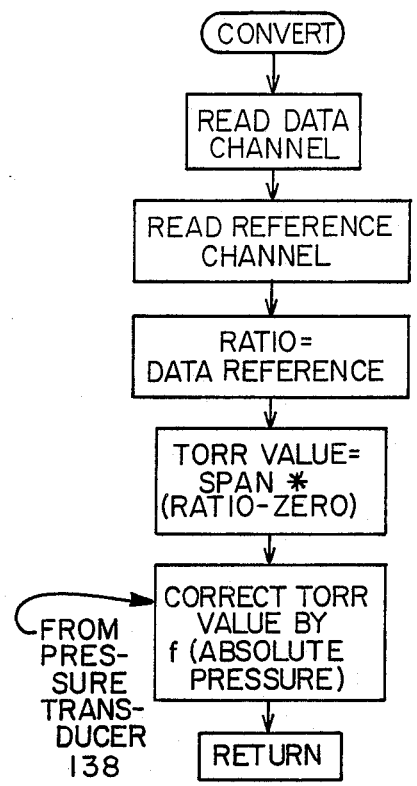
FIG. 8 is a flow diagram showing how pressure compensation is provided in accord with the principles of our invention.

We also pointed out above that microprocessor furnishes a continually updated pressure compensation factor for the gas concentration value produced by transducer 52. A flow diagram for the routine run by the microprocessor 34 in furnishing the pressure compensation factor is illustrated in FIG. 8. As shown in that figure, microprocessor 34 generates a ratio between the pressure as read by transducer 138 and a reference value and converts this ratio to a pressure measured in torrs. This value is corrected by the input from transducer 138 to produce the wanted barometric compensation.

The exemplary system illustrated in the drawing and described above is a stand alone unit. However, it will be obvious to those to whom this specification is addressed that the system could equally well be furnished as an integral part of a larger unit—for example, a gas analyzer as disclosed in copending application Nos. 024,769 and 024,770. In that case, the functions performed by the microprocessor 34 of sampling system 20 would instead be performed by the microprocessor of the gas analyzer, eliminating microprocessor 34 and its cost.

Variations may of course be made in the representative sampling attachment 20 to particularly adapt that attachment to specific applications of our invention. For example, pressure tap 140 may be replaced with a pressure tap 148 on the downstream boss 58 of sampling cuvette 24 so that the output signal from transducer 138 will accurately reflect the pressure on the gases flowing through the cuvette. As another example, switch 32 may be relocated to the vicinity of the cuvette. In this case, it might be operated by the coupling of Luer fitting component 120 to the cuvette instead of the connecting together of Luer fitting components 124 and 126.

The invention may be embodied in still other specific forms without departing from the spirit or essential characteristics thereof. The present embodiments are therefore to be considered in all respects as illustrative and not restrictive, the scope of the invention being indicated by the appended claims rather than by the foregoing description; and all changes which come within the meaning and range of equivalency of the claims are therefore intended to be embraced therein.

What we claim as our invention is:

1. A system for effecting and monitoring the flow of a gas mixture through a gas analyzer sampling device comprising: a first line for connecting the input of the sampling device to the source of the gases being monitored, pump means, a second line for connecting the output of the sampling device to said pump means, and first and second complementary control means mounted on said sampling unit and operatively connected to said pump means which is operable to keep said pump means from being turned on unless a sampling unit having said first control means is connected to said pump means.

2. A system as defined in claim 1 in which said second control means comprises a switch means which can be closed to activate an operating circuit for said pump means and said first control means comprises a fitting on the sampling device which is engageable with the switch means.

3. A system as defined in claim 2 wherein said sampling device is removably coupled between said first and second lines and has a single input opening and a single output opening, a single sampling passage extending between said input opening and said output opening and communicating with said first and second lines, and means providing an optical path which intersects said sampling passage and is adapted to be traversed by a beam of infrared radiation, said infrared radiation being attenuated in a measure which is a predetermined function of the concentration of the gas drawn into said sampling passage by said pump means.

4. A system as defined in claim 3 in which said sampling device has windows at the opposite ends of the passage providing the optical path through said device, said windows being transparent to the energy beamed along said optical path.

5. A system as defined in claim 3 wherein the diameter of the passage in said sampling device is a fraction of the diameter of the passage providing the optical path.

6. A system as defined in claim 3 wherein said first line is fabricated of a material which is permeable to moisture but not to gases to permit the escape of moisture mixed with the gases being monitored from said first line and prevent them from interfering with the analysis of said gases in said sampling device.

7. A system as defined in claim 3 which has a trap in said second line for removing moisture from the gases flowing therethrough to keep said moisture from contaminating components downstream from said second line and/or damaging said pump means.

8. A system as defined in claim 3 which has means for so fixing said sampling device to another object as to relieve the strain on said first line.

9. A system for effecting and monitoring the flow of a gas mixture through a gas analyzer sampling device, said system comprising: a first line for connecting the input of the sampling device to the source of the gases being monitored; pump means; a sampling device removably coupled between said first and second lines, said sampling device having a passage for the gases being analyzed extending therethrough and communicating with said first and second lines; and means including a pressure transducer in line between said pump means and said sampling device for monitoring the pressure on the gases flowing through said system and interrupting the operation of the pump means if said pressure falls below a specified level.

10. A system as defined in claim 9 in which the means for monitoring the pressure on the gases flowing through said system and interrupting the operation of the pump means if said pressure falls below a specified level is adapted to both turn off said pump means and activate a signal if the signal available from said pressure transducer is one that is indicative of an abnormal pressure condition in the system.

11. A system as defined in claim 9 which also has a nasal cannula and wherein: said sampling device has one passage through which said exhaled gases can flow, a second passage which intersects said first passage and provides an optical path for a beam of electromagnetic energy which is attenuatable by said exhaled gases, and first and second, apertured fittings at opposite ends of said first passage; said first line connects said nasal cannula to said first fitting to convey gases exhaled by a subject provided with the cannula to said first passage and through the sampling device; and wherein said second line has one end connected to the second fitting of the sampling device and a second end connected to said pump means.

12. A system as defined in claim 9 wherein said first line is fabricated of a material which is permeable to moisture but not to gases to permit the escape of moisture mixed with the gases exhaled by said first line and prevent interference with the analysis of said gases in said sampling device.

13. A system as defined in claim 9 further comprising a trap in said second line for removing moisture from the gases flowing therethrough to keep said moisture from contaminating components downstream from said second line and/or damaging the pump means.

14. A system as defined claim 9 wherein said first line is a fraction of the length of said second line.

15. A system as defined in claim 9 which has means for so affixing said sampling device to another object as to relieve the strain on said first line.

16. A system as defined in claim 9 in which the sampling device comprises: a member having a single channel for the gases being sampled extending longitudinally therethrough and from end-to-end of the member, fittings at the opposite ends of said member which are adapted to receive said first and second lines; and a passage which extends laterally and completely through said member and intersects said channel to provide an optical path for passing a beam of attenuatable infrared radiation through those gases being analyzed and flowing through said channel, the diameter of said sampling channel being a fraction of the diameter of the passage providing said optical path.

* * * * *